(12) United States Patent
Hernandez

(10) Patent No.: US 11,702,635 B2
(45) Date of Patent: Jul. 18, 2023

(54) HEMATOPOIETIC STEM CELL EXPANSION METHOD

(71) Applicant: PLASTICELL LIMITED, Stevenage (GB)

(72) Inventor: Diana Hernandez, Stevenage (GB)

(73) Assignee: PLASTICELL LIMITED, Stevenage (GB)

( * ) Notice: Subject to any disclaimer, the term of this patent is extended or adjusted under 35 U.S.C. 154(b) by 689 days.

(21) Appl. No.: 16/607,457

(22) PCT Filed: Apr. 25, 2018

(86) PCT No.: PCT/GB2018/051082
§ 371 (c)(1),
(2) Date: Oct. 23, 2019

(87) PCT Pub. No.: WO2018/197868
PCT Pub. Date: Nov. 1, 2018

(65) Prior Publication Data
US 2020/0140817 A1    May 7, 2020

(30) Foreign Application Priority Data
Apr. 25, 2017  (GB) .................................... 1706544

(51) Int. Cl.
*C12N 5/0789* (2010.01)
*C07K 14/705* (2006.01)

(52) U.S. Cl.
CPC ...... *C12N 5/0647* (2013.01); *C07K 14/70503* (2013.01); *C12N 2500/44* (2013.01); *C12N 2501/065* (2013.01)

(58) Field of Classification Search
None
See application file for complete search history.

(56) References Cited

U.S. PATENT DOCUMENTS

| | | | |
|---|---|---|---|
| 3,892,824 A | 7/1975 | Piper et al. | |
| 5,906,984 A * | 5/1999 | Capizzi | A61P 37/04 514/665 |
| 2015/0164952 A1 * | 6/2015 | Mahmud | G01N 33/5023 435/377 |
| 2020/0248143 A1 * | 8/2020 | Rossi | C12N 5/0647 |

FOREIGN PATENT DOCUMENTS

| | | |
|---|---|---|
| EP | 2 755 648 | 7/2014 |
| WO | WO 96/25045 | 8/1996 |
| WO | WO 2004/046312 | 6/2004 |
| WO | WO 2014/189781 | 11/2014 |
| WO | WO 2016/210292 | 12/2016 |

OTHER PUBLICATIONS

List et al., Leukemia, 1998, v.12 pp. 1596-1602.*
Araki et al. (2006) "Expansion of human umbilical cord blood SCID-repopulating cells using chromatin-modifying agents" *Experimental Hematology* 34(2): 140-9.
Excleretal (2014) *Human Vaccines and Immunotherapeutics*, 10 (6),1734-1746.
Gajzer et al. "Epigenetic and molecular signatures of cord blood CD34+ cells treated with histone deacetylase inhibitors" *Vox Sanguinis.* 110(1),79-89, 2016.
List "Hematopoietic stimulation by amifostine and sodium phenylbutyrate: what is the potential in MDS" *Leukemia Research*, 22; S7-S12, 1998.
List et al. "Amifostine stimulates formation of multipotent and erythroid bone marrow progenitors" *Leukemia.* 12; 1596-1602,1998.
Ryoo et al. "Ex vivo culture and amifostine effects in human cord blood" 48th *Annual Meeting of the American Society of Hematology* (Abstract), 2006.
Tatetsu et al. "SALL4 is a key factor in HDAC Inhibitor mediated ex vivo expansion of human peripheral blood mobilized stem/progenitor CD34+CD90+cells", 56th *Annual Meeting of the American Society of Hematology* (Abstract), 2014.
International Search Report and Written Opinion, issued in PCT/GB2018/051082, dated Jun. 26, 2018.
Calloni, et al., "Reviewing and updating the major molecular markers for stem cells," *Stem Cells and Development*, 22:1455-76, 2013.
Chaurasia, et al., "Epigenetic reprogramming induces the expansion of cord blood stem cells," *Am. Soc. Clin. Invest.*, 124:2378-95, 2014.
Mahmud, et al., "Differential effects of epigenetic modifiers on the expansion and maintenance of human cord blood stem/progenitor cells," *Biol. Blood Marrow Transplant*, 20:480-9, 2014.

* cited by examiner

*Primary Examiner* — Michail A Belyavskyi
(74) *Attorney, Agent, or Firm* — Parker Highlander PLLC

(57) ABSTRACT

A method to expand hematopoietic stem and progenitor cells (HSPC) wherein the method comprises obtaining an isolated population of HSPC the culturing the isolated population of HSPC in the presence of a histone deacetylase inhibitor (HDAC inhibitor), to form a cultured population, then adding an aminothiol compound to the cultured population.

19 Claims, 14 Drawing Sheets

Figure 2. Percentage of CD34+/CD133+ cells

Figure 4. GEMM colonies/sample

HEMATOPOIETIC STEM CELL EXPANSION METHOD

This application is a national phase application under 35 U.S.C. § 371 of International Application No. PCT/GB2018/051082, filed Apr. 25, 2018, which claims the benefit of United Kingdom Patent Application No. 1706544.2, filed Apr. 25, 2017, the entirety of each of which is incorporated herein by reference.

FIELD OF THE INVENTION

The present invention relates to a methodology for expanding hematopoietic stem and progenitor cells.

BACKGROUND TO THE INVENTION

Haematopoietic stem and progenitor cell transplantation (HSCT) is the most successful and widely used stem cell therapy to date. HSCT is used to treat conditions where the resident immune system has been compromised, such as in blood disorders or chemo-radiotherapeutic treatment. The use of HSCT is also being clinically proven in gene therapies and is expected to be further extended with new genome editing technologies. Nevertheless challenges still exist, as the transplants have to be tissue matched to the recipients, making demand higher than supply.

Initially, hematopoeitic stem and progenitor cells (HSPC) for transplantation were derived from bone marrow (BM) only. More recently, it was discovered that umbilical cord blood (UCB) also contains HSPC able to engraft in the bone marrow and produce blood cells throughout the lifespan of the recipient. Using UCB as a source of HSPC for use in HSCT has several advantages over more conventional BM; UCB is tested and banked ahead of use and therefore more readily available, UCB also contains more immature stem cells and shows less associated graft versus host disease due to incompatilility of tissue types. However transplants using cells derived from UCB are limited by the number of cells present in one UCB unit. This quantitative limitation cannot be overcome by the transplantation of multiple UCB units into a single subject because of the predominating engraftment of HSPC from one UCB unit only. Therefore to date, these transplants have been restricted to use in small children.

Before transplantation, whole cord blood units are firstly separated to discard red blood cells and subsequently the nucleated cells are further enriched by sorting for either CD34+ cells or CD133+ cells. The marker CD133 is found amongst numerous progenitor/stem cells including those of the hematopoietic system. Further it has been demonstrated that it is the CD133+ compartment of hematopoietic cells where the long term repopulating cells reside. Therefore, by increasing the number of these specific cell types it would greatly enhance engraftment and allow UCB HSCT to be applicable for to treat older children and adults. Unfortunately using conventional culture methods, HSC characterised by the expression of markers CD133, CD34, CD90 and CD49f, are rapidly depleted as they proliferate and concomitantly differentiate into cell types with restricted potency. As such there has been much interest in developing culture conditions which allow the expansion of these HSC, without compromising their stem cell characteristics.

Several stategies exist to increase the total number of cells in UCB units by trying to mimic the niche or environment where these cells normally reside. In the 1970s it was established that conditions containing serum and specific cytokines, mainly stem cell factor (SCF), thrombopoietin (TPO), interlukin-3 (IL3), Interlukin-6 (IL6) and granulocyte colony stimulating factor (G-CSF) could be used for the expansion of HSC in vitro. By the early 90s the first clinical trial using UCB cells expanded in serum-free media containing SCF, G-CSF and MGDF for 10 days, was performed. This expansion method resulted in a 56 fold expansion for the total nucleated cells (TNC) and 4 fold expansion for the CD34+ cells. Patients were infused with one manipulated and one unmanipulated fraction either together or 10 days apart. This trial demonstrated the feasibility of expanding UCB units ex-vivo, and their overall safety. Of the 37 patients treated all showed engraftment, though only 12 were still alive after 30 months. Further work using different combinations of cytokines has led to more defined protocols for in vitro expansion, some of which have shown promise in pre-clinical models. These include the use of SCF, TPO, fms-like tyrosine kinase 3-ligand (FLT3LG), IL3 and IL6, and more recently Wnt1, bone morphogenetic protein 7 (BMP7), angiopoietin-like 5 ANGPTLS and insulin growth factor binding protein 2 (IGFBP2).

Early observations during the in vitro expansion of hematopoeitic cells demonstrated that the accelerated proliferation of cells was associated with a concommital differentiation of these cells into more commited precursors or more terminally differentiated cells. This led to the hypothesis that the fate commitment is most likely controlled at the epigenetic level, with specific sets of genes being transcribed or silenced at different stages. Hence controlling or altering the epigenome would have consequences on the overall phenotype of the cells and their behaviour. Investigations using histone modifiers including histone deacetylase inhibitors yielded promising results. The first of such studies used 5aza 2'deoxycytidine and trichostatin A. Using this regime UCB CD34+/CD90+ cells expanded 4 fold more than cells expanded on cytokines alone and further retained the ability to repopulate NOD/SCID mice. Extension of these studies to include alternative histone modifying enzymes revealed that other HDAC inhibitors also had similar properties, amongst these valproic acid and scriptaid were particularly effective. This was reported by Chaurasia, P. & Hoffman, R. in "Enriched and expanded human cord blood stem cells for treatment of hematological disorders" (2014), Araki, H. et al. "Expansion of human umbilical cord blood SCID-repopulating cells using chromatin-modifying agents" (2006), and also in WO 2014/189781.

Chemical library screens to find molecules which preferentially allow the expansion of CD34+ cells and prevent their differentiation have yielded several molecules of interest. Of note is the aryl hydrocarbon receptor antagonist StemRegeninl, which is currently being used to expand cells in clinical trials. Another set of compounds of note are the pyrimidoindole derivatives UM729 and UM171, which were found to preferentially expand HSCs as determined by the presence of the markers CD34, CD90 (Thy1), and CD49f and the absence of CD38 and CD45RA. Other molecules found to preferentially expand CD34+ cells include resveratrol, GSK-3-inhibitors, p18 protein inhibitors and others.

Amifostine, the prodrug of WR1065, was developed as a radioprotectant compound by the US military and approved for clinical use in 1995 under the name Ethyol. The exact mechanisms by which the drug exerts its effects are still being studied, but it is metabolised in vivo into WR1065, a ROS scavenger, that prevents DNA damage through the activation of p53. Studies of the action of this compound on hematopoietic cells in vitro, showed that pre-treatment of bone marrow derived CD34+ cells with WR1065 enhanced the formation of both CFU-GEMM and BFU-E colonies by as much as 38 fold.

WO9625045 discloses thiols including amifostine for haematopoietic stem cell growth.

SUMMARY OF THE INVENTION

It has been surprisingly found that it is possible to achieve an expansion of HSPC by culturing the cells in the presence of a combination of a HDAC inhibitor, for example scriptaid, and an aminothiol compound such as WR1065. The present invention is based at least in part on data presented herein. A key feature of the present invention is that the cells are cultured in the presence of the HDAC inhibitor to form a cultured population and then, subsequently, the aminothiol compound is added to the cultured population. This method produces expanded cells wherein the number of the total nucleated cells is increased.

It has been found that the method of the invention produces expanded cells showing an enrichment for the subset of cells which are HSC.

Synergy has been observed by using a combination of a HDAC inhibitor and WR1065, an aminothiol compound. The fold expansion of the HSC is more than the additive effect of culturing HSPC in the presence of a HDAC inhibitor alone or WR1065 alone. Data presented herein show that this synergistic effect can produce expanded cells with an enrichment of HSC up to 500 fold.

Therefore, the first aspect of the present invention relates to a method to expand hematopoietic stem and progenitor cells (HSPC) wherein the method comprises;
  i) obtaining an isolated population of HSPC
  ii) culturing the isolated population of HSPC in the presence of a histone deacetylase inhibitor (HDAC inhibitor), to form a cultured population
  iii) adding an aminothiol compound having the formula $RNH(C_nH_{2n})NH(C_nH_{2n})SX$, wherein R is hydrogen, an aryl, an acyl, or an alkyl group containing from 1 to 7 carbon atoms, each n has a value of from 2 to 6 and X is H or $PO_3H_2$; or a pharmaceutically acceptable salt thereof, to the cultured population of HSPC to form expanded cells.

A second aspect is a kit for the expansion of HSPC as defined above, wherein the kit comprises; sterile elements for the expansion of HSPC, a HDAC inhibitor and an aminothiol compound having the formula $RNH(C_nH_{2n})NH(C_nH_{2n})SX$, wherein R is hydrogen, an aryl, an acyl, or an alkyl group containing from 1 to 7 carbon atoms, each n has a value of from 2 to 6 and X is H or $PO_3H_2$; or a pharmaceutically acceptable salt thereof.

A third aspect is an expanded population of cells, preferably HSCs, wherein the expanded population is enriched for Lin-, CD38, CD34+, CD133+, CD45RA-, CD90+ and CD49f+.

A fourth aspect is an expanded population of cells obtainable by the method as described above.

(LMK 10 nM), media supplemented with cytokines, 10 nM LMK235 and WR1065 (LMK 10 nM+WR), media supplemented with cytokines and 50 nM LMK235 (LMK 50 nM), media supplemented with cytokines, 50 nM LMK235 and WR1065 (LMK 50 nM+WR).

Figure 10:
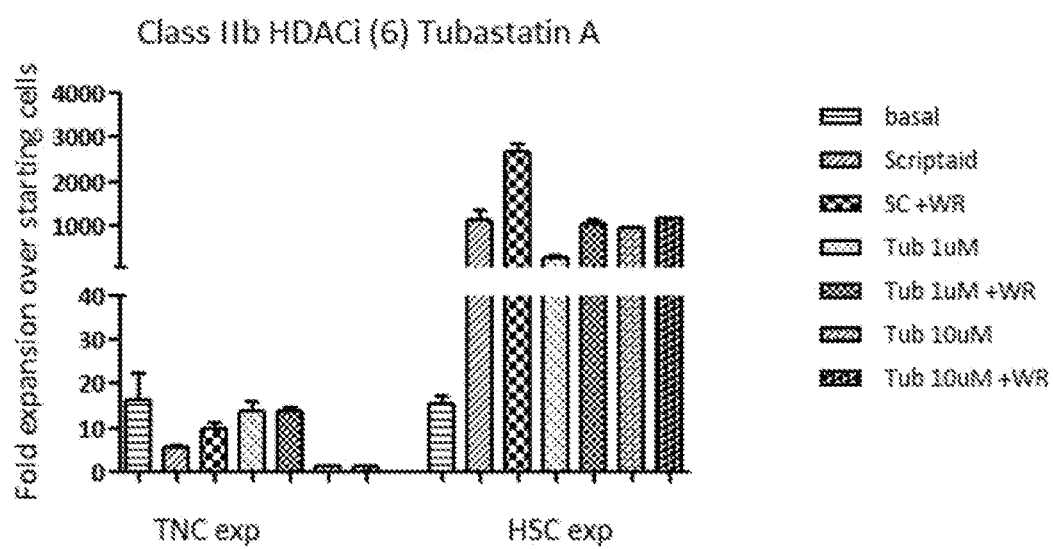

FIG. 10 shows the effect of the class IIb HDAC inhibitor Tubastatin A on cell expansion. The fold expansion of TNC and HSC is shown for cells grown under the conditions; media supplemented with cytokines (basal), media supplement with cytokines and scriptaid (scriptaid), media supplemented with cytokines, scriptaid and WR1065 (SC+WR), media supplemented with cytokines and 1 µM Tubastatin A (Tub 1 µM), media supplemented with cytokines, 1 µM Tubastatin A and WR1065 (Tub 1 µM+WR), media supplemented with cytokines and 10 µM Tubastatin A (Tub 10 µM), media supplemented with cytokines, 10 µM Tubastatin A and WR1065 (Tub 10 µM+WR).

Figure 11:
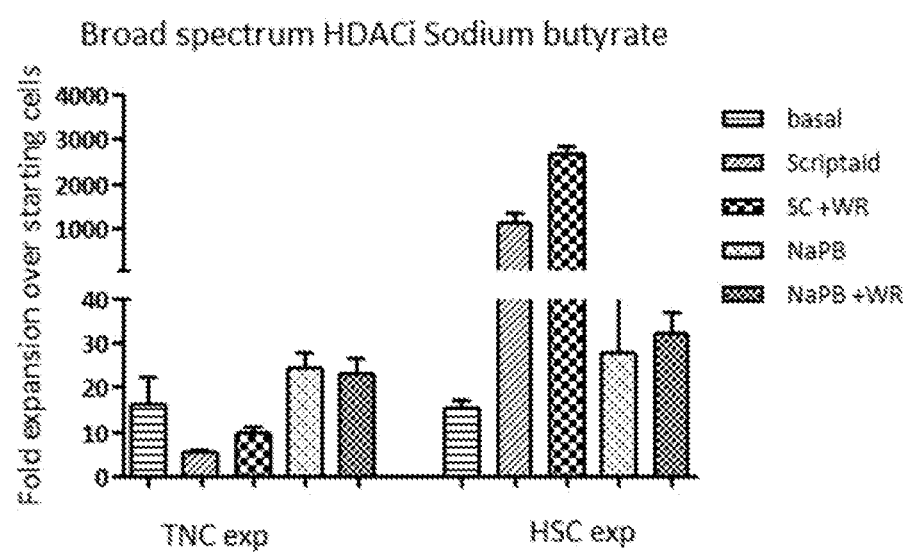

FIG. 11 shows the effect of the broad spectrum HDAC inhibitor sodium phenylbutyrate on cell expansion. The fold expansion of TNC and HSC is shown for cells grown under the conditions; media supplemented with cytokines (basal), media supplement with cytokines and scriptaid (scriptaid), media supplemented with cytokines, scriptaid and WR1065 (SC+WR), media supplemented with cytokines and sodium phenylbutyrate (NaPB), media supplemented with cytokines, sodium phenylbutyrate and WR1065 (NaPB+WR).

Figure 12:
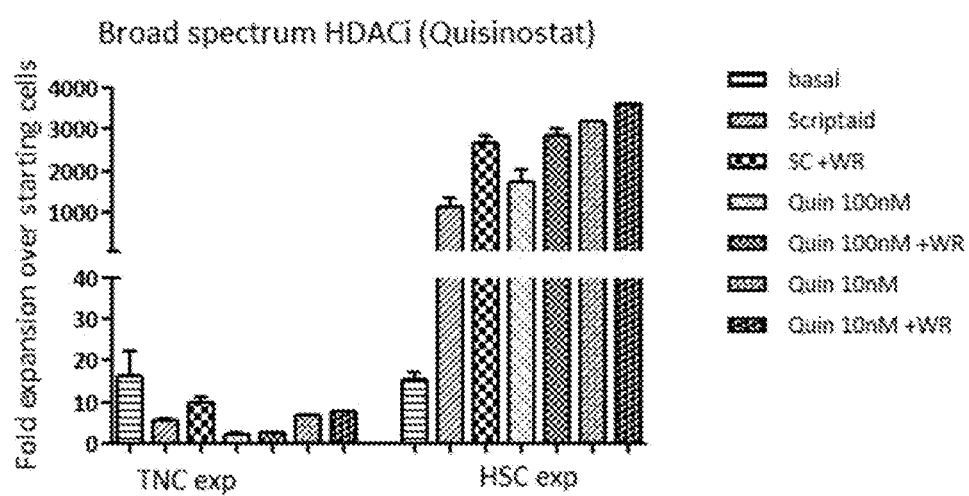

FIG. 12 shows the effect of the broad spectrum HDAC inhibitor quisinostat on cell expansion. The fold expansion of TNC and HSC is shown for cells grown under the conditions; media supplemented with cytokines (basal), media supplement with cytokines and scriptaid (scriptaid), media supplemented with cytokines, scriptaid and WR1065 (SC+WR), media supplemented with cytokines and 100 nM quisinostat (Quin 100 nM), media supplemented with cytokines, 100 nM quisinostat and WR1065 (Quin 100 nM+WR), media supplemented with cytokines and 10 nM quisinostat (Quin 10 nM), media supplemented with cytokines, 10 nM quisinostat and WR1065 (Quin 10 nM+WR).

Figure 13:
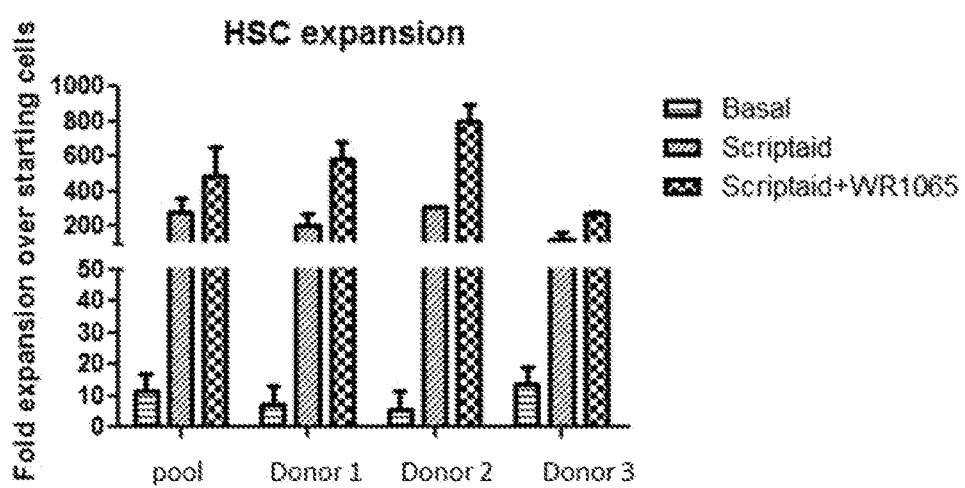

FIG. 13 shows the reproducibility of the cell expansion protocol using basal media, scriptaid and the combination treatment of scriptaid and WR1065. The fold expansion of HSC is shown for cells from three separate donors and a pooled sample of cells.

Figure 14:
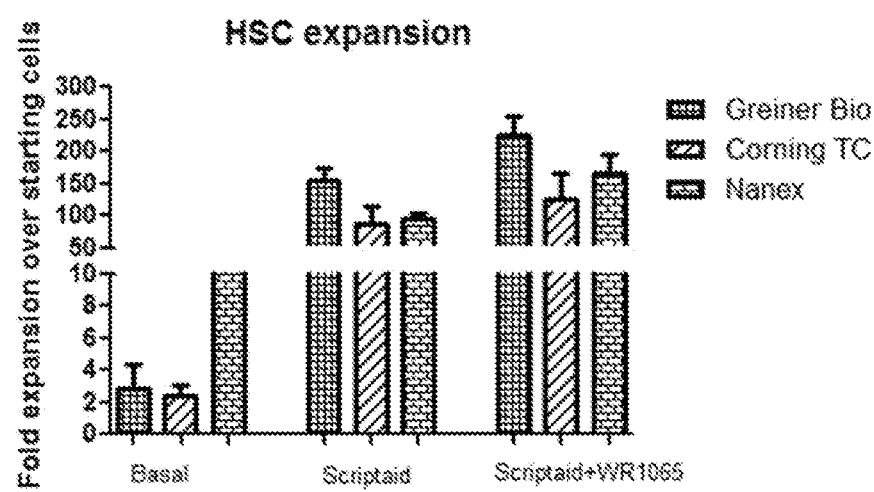

FIG. 14 shows the fold expansion in HSC when the cells were expanded on the different culture plates; Nanex scaffolds, TC treated Corning 24 well plates or suspension Greiner Bio 24 well plates

DETAILED DESCRIPTION OF THE INVENTION

As used herein the term hematopoietic stem and progenitor cells (HSPC) refers to cells found in bone marrow, umbilical cord blood and peripheral blood which can differentiate and/or proliferate to form blood cells, examples of blood cells include, but is not restricted to, monocytes, macrophages, neutrophils, basophils, eosinophils, erythrocytes, dendritic cells, megakaryocytes, platelets, T cells, B cells, and natural killer cells.

As used herein the term "hematopoietic stem cells" or "HSC" refers to multipotent or pluripotent cells which have the ability to differentiate into blood cells of all lineages and to regenerate themselves whilst maintaining their pluripotent characteristics. The term "HSC" as used herein refers to cells which are; Lin−, CD38−, CD34+, CD133+, CD45RA−, CD90+ and CD49f+. Within the terms "CD34+", "CD133+", "CD90+", "CD49f+" the (+) designation indicates that the specified cluster of differentiation (CD) is expressed by the cell and is present on the cell surface. Within the terms "CD38−", "CD45RA−" the (−) designation indicates that the specified CD is not expressed or poorly expressed by the cell. However, human embryonic stem cells and any cell resulting from the destruction of a human embryo are not within the scope of the invention.

As used herein the term "isolated population" refers to a sample of cells which has been obtained from a source. Wherein the cells may have been obtained commercially, or wherein the cells were obtained from a subject. The source of an isolated population includes, but is not restricted to, umbilical cord blood, bone marrow and peripheral blood. The "isolated population" may have been obtained from a source which is fresh or frozen, wherein a fresh source has not been frozen prior to use. If the sample is frozen then the cells will be thawed before use in the method.

As used herein the term "cultured population" refers to an isolated population of cells which has been propagated in an artificial medium ex vivo. It will be obvious to a skilled person what type of artificial media to use, an example of a suitable media is StemSpan ACF media (Stem Cell Technologies). The artificial media may also be supplemented with other factors or cytokines to improve the growth of the cells, examples of supplements include, but are not restricted to, stem cell factor (SCF), fms-related tyrosine kinase 3-ligand (FLT3LG) and thrombopoietin (TPO). The isolated population can be cultured/propagated over a number of days to form a cultured population. In some embodiments, the culturing time is from 2 to 20 days, more preferably 3 to 20, most preferably 4 to 15 days. For example the culturing/propagating can take place over 20, 15, 10, 9, 8, 7, 6, 5 or 4 days. The total culturing time encompasses the time taken to perform steps (ii) and (iii).

The term histone deacetylase inhibitor (HDAC inhibitor) as used herein refers to a compound which inhibits the activity of the enzyme histone deacetylase. There are four classifications of histone deacetylase; class I, class II, class III, and class IV. Based on their sequence homology and domain organisation, class II inhibitors can be further subdivided into class IIa and class IIb. As used herein the term histone deacetylase refers to compound which can inhibit the activity of any of the classes of histone deacetylase.

Examples of HDAC inhibitors include, but are not restricted to, Scriptaid, Vorinostat, Tacedinaline, RG2833, RGFP966, Trichostatin A, LMK235, Tubastatin A, Quisinostat, LBH589, PXD101, ITF2357, PCI-24781, FK228 MS-275, MGCD0103, Sodium Phenylbutyrate, Valproic acid, AN-9, Baceca, Savicol.

An aspect of the invention includes the use of an aminothiol compound having the formula $RNH(C_nH_{2n})NH(C_nH_{2n})SX$, wherein R is hydrogen, an aryl, an acyl, or an alkyl group containing from 1 to 7 carbon atoms, each n has a value of from 2 to 6 and X is H or $PO_3H_2$; or a pharmaceutically acceptable salt thereof.

As used herein, "aryl" means a monocyclic, bicyclic, or tricyclic monovalent or divalent (as appropriate) aromatic radical, such as phenyl, biphenyl, naphthyl, anthracenyl, which can be optionally substituted with up to five substituents preferably selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, "alkyl" means a $C_1$-$C_7$ alkyl group, which can be linear or branched. Preferably, it is a $C_1$-$C_6$ alkyl moiety. More preferably, it is a $C_1$-$C_4$ alkyl moiety. Examples include methyl, ethyl, n-propyl and t-butyl. It may be divalent, e.g. propylene.

As used herein, acyl is an alkyl group as defined above, which includes a carbonyl group (C=O).

Each of the alkyl and acyl groups may be optionally substituted with aryl, cycloalkyl (preferably $C_3$-$C_{10}$) or heteroaryl. They may also be substituted with halogen (e.g. F, Cl), $NH_2$, $NO_2$ or hydroxyl.

As used herein the term "umbilical cord blood" has its conventional use in the art; that is generally the blood that is left in the umbilical cord and placenta post-partum. Human cord blood is within the scope of the present invention and is obtained with written informed pre-consent and ethical approval.

As used herein the term "peripheral blood" has its conventional use in the art; that is generally blood which is circulating throughout the circulatory system. Human peripheral blood is within the scope of the present invention and is obtained with written informed pre-consent and ethical approval.

As used herein the term "bone marrow" has its conventional use in the art; that is, generally the gelatinous tissue present in bone cavities. The tissue comprises red bone marrow, a subset of bone marrow having populations of hematopoietic stem cells, progenitor cells and precursor cells. Human bone marrow is within the scope of the present invention and is obtained with written informed pre-consent and ethical approval.

As used herein the term "expanded cells" refers to cells which have been cultured ex vivo, under appropriate conditions, and undergone cell division to amplify the number of cells. As used herein the term "cell expansion" refers to the amplification of the number of cells by the ex vivo culturing of cells under appropriate conditions, wherein the number of cells present at the end of culturing is greater than the number of cells present at the start of culturing.

Within the cells, wherein the cells may be part of the isolated population of cells, the cultured population of cells or the expanded cells, there are subtypes of cells. Examples of the cell subtypes are, but not restricted to; hematopoietic stem cells, hematopoietic progenitor cells and cells as defined by their phenotypic markers. Non-limiting examples of phenotypic markers are; Lin or CD38 or CD34 or CD133 or CD45RA or CD90 or CD49f, wherein the cells can also be defined by combinations of these phenotypic markers. As used herein the term "enriched" is used to refer to a set of cells which contains a high proportion of a specific subset/subtype of cell, wherein the set of cells may contain 2%, or 5%, or 10%, or 15%, or 20%, or 25%, or 30%, or 35%, or 40%, or 45%, or 50%, or 55%, or 60%, or 65%, or 70%, or 75%, or 80%, or 85%, or 90% of the specific subset/subtype of cell. Within the present invention the term "enriched" can be used to refer to a population of cells wherein the cells have undergone expansion and wherein a specific subtype of cells have increased in number proportionally more than other cells within the population. This enriched population of cells contains a significant proportion of a specific subtype of cells, wherein the significant proportion may be 2%, or 5%, or 10%, or 15%, or 20%, or 25%, or 30%, or 35%, or 40%, or 45%, or 50%, or 55%, or 60%, or 65%, or 70%, or 75%, or 80%, or 85%, or 90% of the total population.

As used herein the term "serum free tissue culture system" refers to culturing cells in a media which has not been supplemented with serum derived from an animal.

As used herein the term "feeder free tissue culture system" refers to a method of culturing cells without utilising a layer of connective tissue cells to support and provide metabolites to the growing cells.

As used herein the term "total cell expansion" refers to the increase in number of total nucleated cells.

As used herein the term "total culturing time" refers to the time in which steps ii) and iii) are carried out. Wherein step ii) comprises culturing the isolated population of HSPC in the presence of a histone deacetylase inhibitor (HDAC inhibitor), to form a cultured population, and step iii) comprises adding an aminothiol compound having the formula $RNH(C_nH_{2n})NH(C_nH_{2n})SX$, wherein R is hydrogen, an aryl, an acyl, or an alkyl group containing from 1 to 7 carbon atoms, each n has a value of from 2 to 6 and X is H or $PO_3H_2$; or a pharmaceutically acceptable salt thereof, to the cultured population of HSPC to form expanded cells. During the total culturing time the cells are allowed to grow on an appropriate media supplemented with a HDAC inhibitor, the end of the total culturing time is signified by the cells being harvested/pooled/analysed.

An aspect of the present invention is a method to expand hematopoietic stem and progenitor cells (HSPC) wherein the method comprises;

i) obtaining an isolated population of HSPC ii) culturing the isolated population of HSPC in the presence of a histone deacetylase inhibitor (HDAC inhibitor), to form a cultured population iii) adding an aminothiol compound having the formula $RNH(C_nH_{2n})NH(C_nH_{2n})SX$, wherein R is hydrogen, an aryl, an acyl, or an alkyl group containing from 1 to 7 carbon atoms, each n has a value of from 2 to 6 and X is H or $PO_3H_2$; or a pharmaceutically acceptable salt thereof, to the cultured population of HSPC to form expanded cells.

In an embodiment of the present invention, step i) further comprises selecting for cells which are CD133+. In some embodiments, the isolated population comprises cells which are CD133+. In an embodiment step i) further comprises selecting for cells which are CD34+. If the isolated population of HSPC is obtained from a source that has been frozen it may be preferable to select for cells which are CD34+. If the isolated population of HSPC is obtained from a fresh source then it may be preferable to select for cells which are CD133+. Suitable methods for selecting cells by cell surface markers are known in the art for example using Magnetic Activated Cell Sorting (MACs) or Fluorescent Activated Cell Sorting (FACS). Preferably, the isolated population comprises cells which are CD38− or CD34+ or CD133+ or CD45RA− or CD90+ or CD49f+, or any combination thereof.

In one embodiment of the present invention, the isolated population of cells is obtained from umbilical cord blood or bone marrow or peripheral blood. In a preferred embodiment, the isolated population of cells is obtained from umbilical cord blood. In some embodiments, the cells are obtained from a mammal (for example mouse, rat, dog or human). A preferred embodiment is wherein the cells are obtained from a human.

In one embodiment of the present invention the HDAC inhibitor is selected from a broad-spectrum inhibitor, or a selective class I, class IIa, class IIb, class III or class IV inhibitor. Preferably, the HDAC inhibitor is selected from a broad-spectrum inhibitor, or a selective class I, class IIa, class III or class IV inhibitor. More preferably, the HDAC inhibitor is a broad-spectrum inhibitor, class I or class IIa inhibitor.

In a preferred embodiment, the HDAC inhibitor is selected from scriptaid, RG2833, RGFP966, LMK235, Tubastatin A, quisinostat, sodium phenylbutyrate. In some embodiments of the present invention, the HDAC inhibitor is a scriptaid or quisinostat. In a preferred embodiment the HDAC inhibitor is scriptaid, which has the structure;

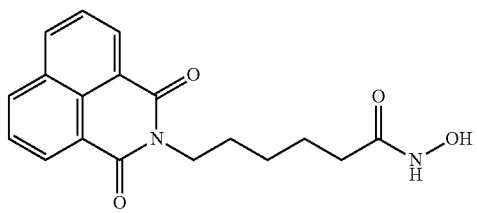 [SMILES: O=C(CCCCCN1C(=O)c2cccc3cccc(c23)C1=O)NO]

An aminothiol compound of the invention has the formula $RNH(C_nH_{2n})NH(C_nH_{2n})SX$, wherein R is hydrogen, an aryl, an acyl, or an alkyl group containing from 1 to 7 carbon atoms, each n has a value of from 2 to 6 and X is H or $PO_3H_2$; or a pharmaceutically acceptable salt thereof.

In a preferred embodiment, R is hydrogen.

In some embodiments, the aminothiol compound of the invention is amofostine:

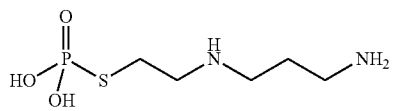

Or
WR1065:

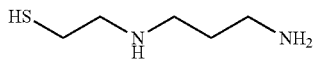

Most preferably, the aminothiol compound is WR1065.

In one embodiment of the present invention the HDAC inhibitor is used at a concentration of between 0.01 µM to 50 µM, preferably between 0.1 µM to 10 µM, more preferably, the HDAC inhibitor is used at a concentration of 1 µM.

In a preferred embodiment of the present invention the aminothiol compound e.g. WR1065, is used at a concentration of 50 µM to 500 µM, preferably 50 µM to 150 µM, more preferably at a concentration of 100 µM.

In a preferred embodiment of the present invention, the HDAC inhibitor is used at a concentration of 1 µM, and preferably the aminothiol compound e.g. WR1065 is used at a concentration of 100 µM.

In some embodiments of the present invention, steps ii) and iii) are performed over two to ten days. In a preferred embodiment steps ii) and iii) are performed over five to 10 days. In a more preferred embodiment steps ii) and iii) are performed over about five days. In an embodiment of the present invention, step iii) begins up to 48 hours before the end of the total culturing time (i.e. the end of step (iii)). In some embodiments of the present invention step iii) begins 16 to 20 hours before the end of the total culturing time. Preferably, steps ii) and iii) are performed over five days and, more preferably, step iii) is performed 16 to 20 hours before the end of the total culturing time.

Preferably, in the present invention, step ii) is performed over 4 to 10 days. In a preferred embodiment, step ii) is performed over at least 4 days. In some embodiments step iii) is performed after the cells have been cultured with the HDAC inhibitor (according to step ii)) for at least 4 to 10 days, preferably at least 4 days. In some embodiments step iii) is performed after the cells have been cultured as in step ii) for at least 4 to 10 days, preferably at least 4 days. Preferably, step iii) is begins up to 48 hours before the end of the total culturing time.

Preferably, the cells are cultured in a serum free tissue culture system. In some embodiments of the present invention, cells are cultured in a feeder free tissue culture system. Whilst the culture system is serum and/or feeder free, various nutrients may be added to provide adequate growth and expansion conditions for cells. Examples of suitable media include, but are not limited to StemSpan ACF media (Stem Cell Technologies), StemPro34 serum-free medium (Invitrogen), Stemline II (Thermo Fisher), HPC Expansion Medium DXF (PromoCell), QBSF-60 (Quality Biological), StemMACS HSC expansion media XF (Miltenyi Biotec). In a preferred embodiment of the present invention the cells are cultured in StemSpan ACF media (Stem Cell Technologies). Suitable media may also contain various additives and components which may be chemical or biological components. These components may be incorporated into the suitable media singly or in combination and the skilled person will be able to choose suitable components as required. These components may also be incorporated during culture as required. Examples of components both biological and chemical include, but are not restricted to; amino acids, vitamins, cytokines, growth factors, hormones, antibiotics, fatty acids, saccharides, sodium, calcium, potassium, magnesium, phosphorus, agar, agarose, methylcellulose, collagen, insulin, transferrin, lactoferrin, cholesterol, ethanolamine, sodium pyruvate, 2-mercaptoethanol, polyethylene glycol, sodium selenite.

Various cytokines may be incorporated into the media and/or incorporated during culture, examples of suitable cytokines include, but are not restricted to; interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-14 (IL-14), interleukin-15 (IL-15), interleukin-18 (IL-18), interleukin-21 (IL-21), interferon-α (INF-α), interferon-β (INF-β), interferon-γ (INF-γ), granulocyte-macrophage colony stimulating factor (GM-CSF), stem cell factor (SCF), Wnt1, bone morphogenetic protein 7 (BMP7), angiopoietin-like 5 (ANGPTLS), insulin growth factor binding protein 2 (IGFBP2), erythropoietin (EPO), thrombopoietin (TPO), Fms-like tyrosine kinase 3-ligand (FLT3LG). In an embodiment of the present invention the media is supplemented with SCF, TPO and FLT3LG.

Various growth factors may be incorporated into the media and/or incorporated during culture. Examples of suitable growth factors include, but are not restricted to insulin-like growth factor (IGF), epidermal growth factor (EGF), human epidermal growth factor (hEGF), plateletderived growth factor (PDGF), fibroblast growth factor 1 (FGF1), nerve growth factor (NGF), macrophage inflammatory protein 1-α (MIP-1α), leukaemia inhibitory factor (LIF).

In an embodiment of the present invention, the isolated population is cultured at a temperature between 32° C. to 39° C., preferably between 36° C. to 38° C. In an embodiment of the invention the cells are cultured in a humidified incubator with between about 1% to about 50% $CO_2$, preferably between about 1% to about 25% $CO_2$, more preferably between about 1% to about 10% $CO_2$. The present invention can be performed in a culture vessel suitable for animal cell culture. In one embodiment the present invention is performed in Nanex Hematopoietic Stem/Progenitor Cell (HSPC) Expansion Plates or TC treated Corning 24 well plates or suspension Greiner Bio 24 well plates. In a preferred embodiment, the present invention is performed in a conventional cell culture plate or a suitable closed system such as a cell culture bag (e.g VueLife®) or a stirred bioreactor.

In a preferred embodiment of the present invention, the total cell expansion is between about 2-fold to about 50-fold, or from about 2-fold to about 25-fold, or from about 2-fold to about 20-fold. The total cell expansion is determined by measuring the number of total nucleated cells at the start of the culturing time and comparing to the number of total nucleated cells present at the end of the culturing time.

In a preferred embodiment, the expansion of Lin−, CD38−, CD34+, CD133+, CD45RA−, CD90+ and CD49f+ cells is 50 to 800-fold, more preferably 400 to 600-fold, most preferably 500-fold. The expansion of Lin−, CD38−, CD34+, CD133+, CD45RA−, CD90+ and CD49f+ cells is determined by measuring the number of Lin−, CD38−, CD34+, CD133+, CD45RA−, CD90+ and CD49f+ cells present at the start of the culturing time and comparing it to the number of Lin−, CD38−, CD34+, CD133+, CD45RA−, CD90+ and CD49f+ cells present at the end of the culturing time. Suitable methods for determining cell expansion are known in the art and include, for example, multicolour flow cytometric analysis combined with total cell counting, use of absolute counting beads in combination with flow cytometric analysis, cell counts based on imaging analysis of a cell aliquot using a manual or automated hemocytometer (Viacell, Countess, Nucleocounter, Nexcelome)

In some embodiments, the expanded cells are enriched for HSC. In one embodiment the expanded cells are enriched for Lin− or CD38− or CD34+ or CD133+ or CD45RA− or CD90+ or CD49f+ or any combination thereof, preferably wherein the cells are enriched for CD34+, CD133+, more preferably wherein the expanded cells are enriched for CD38−, CD34+, CD133+, most preferably wherein the expanded cells are enriched for Lin−, CD38−, CD34+, CD133+, CD45RA−, CD90+, CD49f+.

An aspect of the present invention is a kit for the expansion of HSPC as defined above, wherein the kit comprises; sterile elements for the expansion of HSPC, a HDAC inhibitor and an aminothiol compound having the formula $RNH(C_nH_{2n})NH(C_nH_{2n})SX$, wherein R is hydrogen, an aryl, an acyl, or an alkyl group containing from 1 to 7 carbon atoms, each n has a value of from 2 to 6 and X is H or $PO_3H_2$; or a pharmaceutically acceptable salt thereof. In a preferred embodiment the kit also contains apparatus and/or materials for obtaining an isolated population of HSPC. A person skilled in the art will know of suitable elements, apparatus and/or materials. Examples include magnetic bead isolation, MACS bead isolation columns, CliniMACS (Miltenyi) or FACS sorting.

The following examples illustrate the invention.

EXAMPLES

Example 1 Expansion of Cells from Umbilical Cord Blood

Materials and Methods
Cell Culture

Human UCB units were collected with written informed pre-consent and ethical approval from Oxford and Berkshire National Research Ethical Committees and studies conducted with approval of the NHSBT research committee. UCB mononuclear cells (MNC) were isolated by density gradient centrifugation on lymphocyte separation medium 1077 (PAA Laboratories, Pasching, Austria; density<1.077 g/ml). CD133+ cells were isolated from the MNC with immunomagnetic beads (Miltenyi Biotec, Germany). After isolation, the cells were cryopreserved in 10% DMSO in FCS (fetal calf serum) and stored at −150° C. in aliquots of $1\times10^5$ cells/vial. Cells were analysed for the purity of the isolation with flow cytometry on a BD LSR II (BD Biosciences, CA) using CD34-APC, CD133-PE and the appropriate isotype controls (all Miltenyi Biotec). Bone marrow derived CD133+ cells were obtained commercially from Lonza and peripheral blood CD133+ cells were isolated using immunomagnetic beads as above from total peripheral blood mononuclear cells obtained commercially from Lonza Biologics.

Vials from 2 or 3 donors were thawed and pooled in StemSpan ACF media (Stem Cell Technologies) containing 100 ng/mL SCF, 100 ng/mL FLT3LG and 20 ng/mL TPO (all from Miltenyi Biotec). After counting, cells were plated in 96 well round bottom suspension plates at 20,000 cells/well in the above media. Cells were allowed to recover overnight in these conditions in a 37° C. humidified incubator with 5% $CO_2$.

The next day cells were harvested from the plates counted, and seeded into 24 well Nanex plates (Compass Biomedical) or standard tissue culture treated plates at 2500 cells/well in 1 mL basal media (StemSpan ACF with 100 ng/mL SCF, 100 ng/mL FLT3LG and 20 ng/mL TPO) containing an HDAC inhibitor (for most experiments scriptaid was used at a concentration of 1 μM). An aliquot of cells was used for CFU analysis and another for flow cytometry analysis.

After 3 days in culture the media was either replaced or supplemented with fresh media with the cytokines (SCF, TPO and FLT3LG) and the HDAC inhibitors (scriptaid 1 μM). Sixteen to twenty hours prior to harvest WR1065 was added at a concentration of 100 μM. After total of 5 days in expansion, cells are harvested, counted and analysed by flow cytometry.

CFU Assays

CFU assays were performed using the MethoCult Classic kit (Stem Cell Technologies) under manufacturer's instructions. Briefly, an aliquot of cells (either known number or volume) was mixed with 3 mL of MethoCult media and plated using a blunt needle and syringe into one well of a 6 well suspension plate. Plates were incubated for 2 weeks at 37° C. in a humidified incubator with 5% CO2 without media change. After 2 weeks, colonies were photographed under a dissecting microscope and counted. The proportion of colonies of different kinds was then scored and the proportion/sample was calculated.

Flow Cytometry Assays

Cells were harvested, washed and stained in 3% FBS in PBS using a panel of pre-conjugated antibodies. Cells were incubated with antibodies on ice for 30 min, then washed twice in 3% FBS in PBS and resuspended in 250 uL of above buffer before being analysed using a BD Canto II flow cytometer. [Antibody panel was as follows: 5 Lin custom cocktail (CD235a, CD4, CD10, CD11b and CD19) APC-Vio770, CD38-PE-Vio770, CD34-PerCP-Vio700, CD133-PE, CD45RA-VioBlue, CD49f-FITC, CD90-APC (all from Miltenyi Biotec).]

Cell Counting

Cell number was measured using flow cytometry with the aid of counting beads (CountBright beads Life Technologies).

Results

Figure 1:
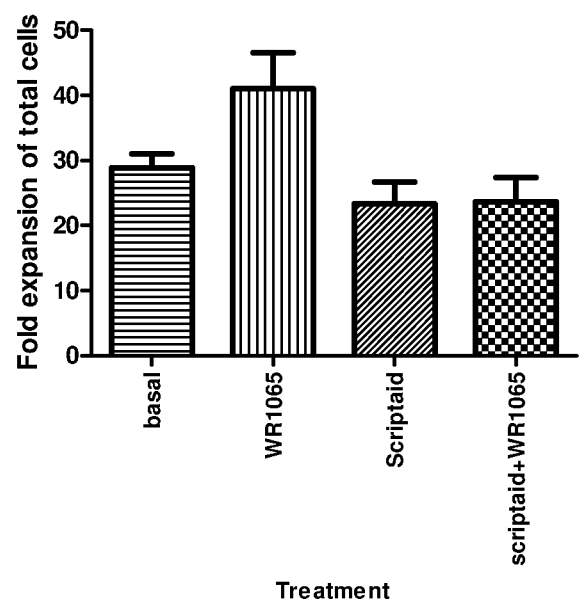
FIG. 1 shows the fold expansion of the total nucleated cells derived from umbilical cord blood, under the conditions; basal media supplemented with cytokines (basal), media supplemented with cytokines and WR1065 (WR 1065), media supplement with cytokines and scriptaid (scriptaid), media supplemented with cytokines, scriptaid and WR1065 (scriptaid+WR1065).
Figure 2:
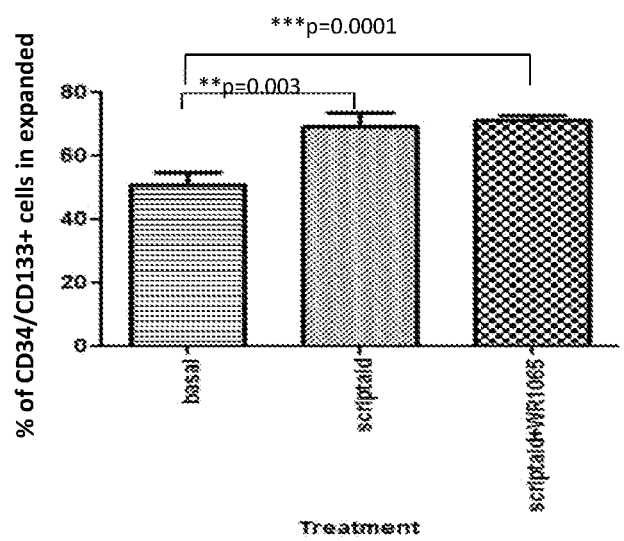
FIG. 2 shows the proportion of CD34+/CD133+ cells present in the expanded populations of cells derived from umbilical cord blood under the conditions; basal media supplemented with cytokines (basal), media supplement with cytokines and scriptaid (scriptaid), media supplemented with cytokines, scriptaid and WR1065 (scriptaid+WR1065).

FIG. 1 shows the analysis of total nucleated cells across all treatment groups shows there is little difference between the expansion of cells in all culture conditions. In a 5 day culture period the expansion of cells in basal media containing cytokines is around 20-40 fold (differences are seen between different donors and different biological repeats), this is slightly reduced in cells grown on scriptaid (1 µM) with cytokines with or without WR1065 (100 µM), but this reduction is not significant. [basal vs scriptaid p=0.191, basal vs scriptaid+WR1065 p=0.28] n=14. However, when comparing the expansion of the CD133+/CD34+ cells (shown in FIG. 3), the cells that have been treated with scriptaid alone and scriptaid in combination with WR1065 show an increase in the proportion of CD133+/CD34+ cells compared to the cells grown on cytokines alone. Analysis of cells prior to ex-vivo culture (FIG. 2) shows that the purity of the starting population is high (between 90-98% CD133+/CD34+). After 5 days in culture in basal media+cytokines (denoted as basal), the proportion declines to around 50%. In cells grown with the combination treatment this proportion remains much higher at around 72%. This difference is statistically significant (p=0.003 and *p=0.0001 respectively).

Figure 3:
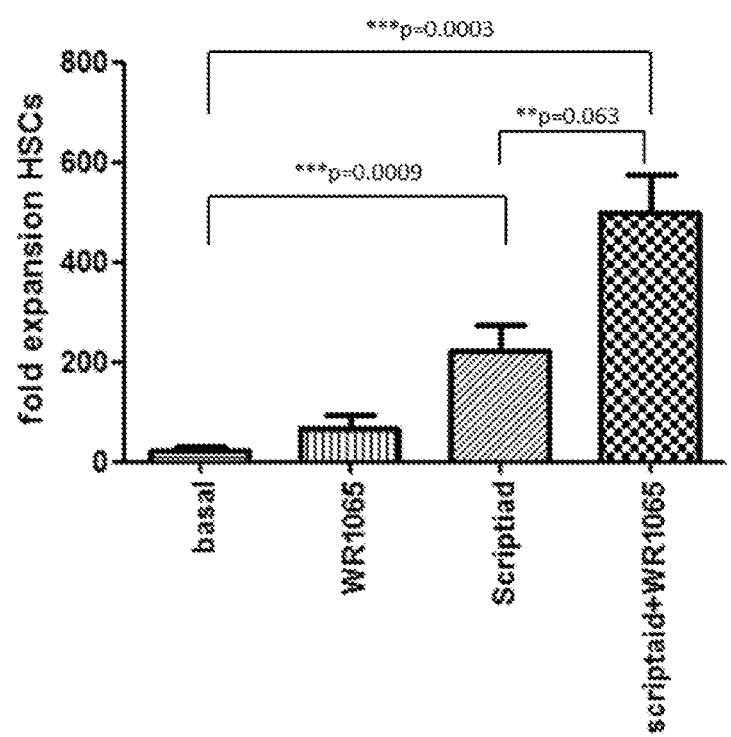
FIG. 3 shows the fold expansion of lin-/CD38-/CD34+/CD45RA-/CD133+/CD90+/CD49f+ cells in the final population of expanded cells derived from umbilical cord blood under the conditions; basal media supplemented with cytokines (basal), media supplemented with cytokines and WR1065 (WR 1065), media supplement with cytokines and scriptaid (scriptaid), media supplemented with cytokines, scriptaid and WR1065 (scriptaid+WR1065).
Figure 4:
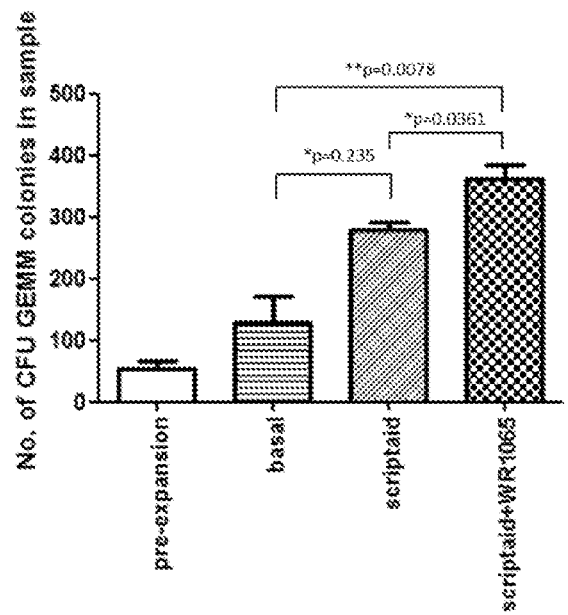
FIG. 4 shows the number of colony-forming units granulocyte, erythrocyte, monocyte, megakaryocyte (CFU-GEMM) colonies present in the final population of expanded cells derived from umbilical cord blood under the conditions; basal media supplemented with cytokines (basal), media supplement with cytokines and scriptaid (scriptaid), media supplemented with cytokines, scriptaid and WR1065 (scriptaid+WR1065).

The fold expansion of the specific HSC-enriched population characterised by the phenotype Lin-, CD38-, CD34+, CD45RA-, CD133+, CD90+, CD49f+, is 20 fold higher in the combination treatment than in cytokines alone. Measurements of the number of cells with the phenotype (Lin-, CD38-, CD34+, CD45RA-, CD133+, CD90+, CD49f+) present at the end of the culture compared to those seeded at the beginning of the expansion can be compared and represented as a "fold expansion". Comparison of the fold expansion shows cells treated with scriptaid have approximately 10 fold higher expansion than the cells grown in the basal media containing cytokines. The cells grown in the combination of scriptaid and WR1065 show a 20-fold higher expansion than the cells grown in the basal media containing cytokines (FIG. 3). This difference is statistically significant. The action of the drug combination is more than the additive effect of each individual compound. Cells grown on cytokines+WR1065 show expansion of the "HSC" compartment of around 3 fold more than cytokines alone, those grown on the scriptaid alone show 10 fold expansion above basal, and the combination shows 20 fold expansion above basal (FIG. 3), therefore this is greater than the additive effect. In vitro culture of UCB derived CD133+ cells with HDAC inhibitor and WR1065 increases the number of colony forming units granulocyte, erythrocyte, monocyte, megakaryocyte (CFU-GEMM) colonies compared to cells grown on cytokines alone. Cells expanded on the combination treatment and plated at limiting dilutions in MethoCult produce 6 to 7 times more GEMM colonies that the pre-expanded cells and at least 2.5 times more than cells expanded in cytokines alone, shown in FIG. 4, this difference is statistically significant.

Example 2 Expansion of Cells from Bone Marrow

Figure 5:
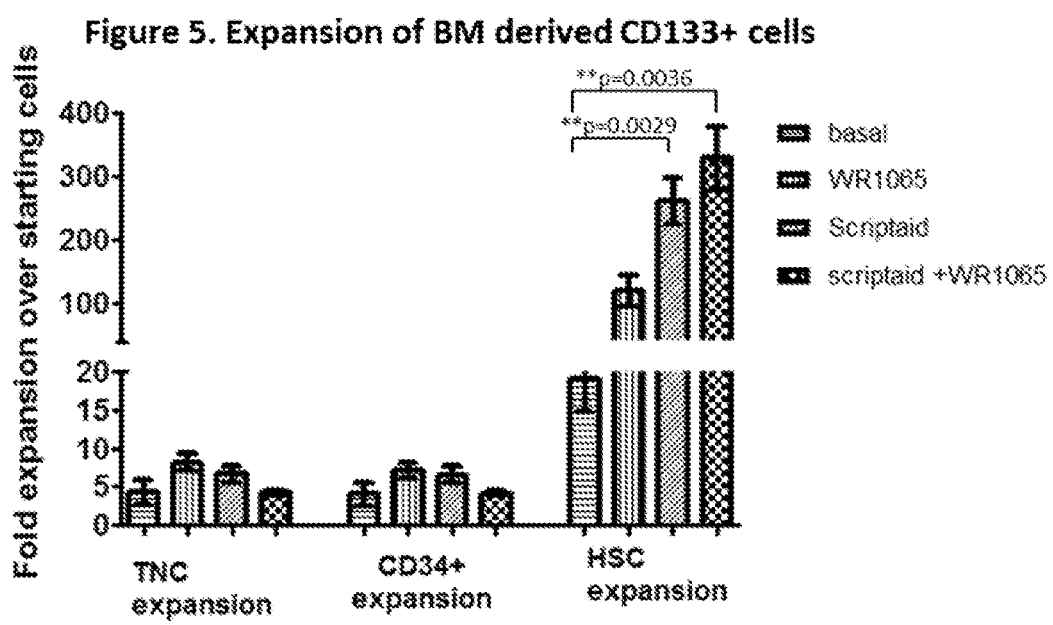
FIG. 5 shows the fold expansion of total nucleated cells, CD34+ cells and HSC derived from bone marrow, when grown under the conditions; media supplemented with cytokines (basal), media supplemented with cytokines and WR1065 (WR 1065), media supplement with cytokines and scriptaid (scriptaid), media supplemented with cytokines, scriptaid and WR1065 (scriptaid+WR1065).

The expansion protocol, as defined above, was also performed on cells derived from bone marrow. Bone marrow cells show a 5 fold expansion of both total nucleated cells and CD34+ cells when cultured in the combination treatment. However, the HSC (characterised by the phenotype Lin-, CD38-, CD34+, CD45RA-, CD133+, CD90+, CD49f+) cell expansion is 17 times higher for the cells grown in scriptaid and WR1065 compared to that of the cells grown in basal media containing cytokines FIG. 5.

Example 3 Expansion of Cells Derived from Peripheral Blood

Figure 6:
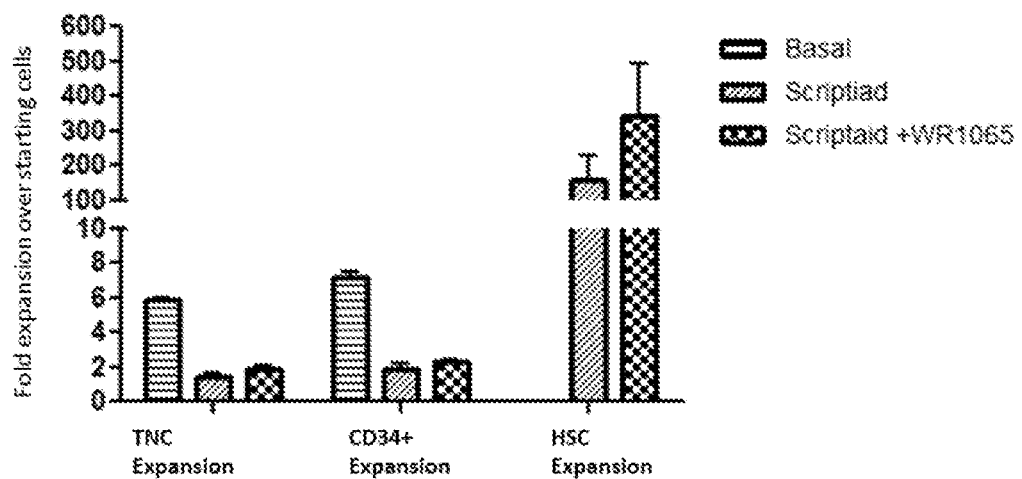
FIG. 6 shows the fold expansion of total nucleated cells, CD34+ cells and HSC derived from peripheral blood, when grown under the conditions; media supplemented with cytokines (basal), media supplemented with cytokines and scriptaid (scriptaid), media supplemented with cytokines, scriptaid and WR1065 (scriptaid+WR1065).

The expansion protocol, as defined above, was also performed on cells derived from peripheral blood. The overall fold expansion of cells derived from peripheral blood was lower than those of cells derived from umbilical cord blood. Peripheral blood cells show a 2-6 fold expansion of both total nucleated cells and CD34+ cells under all growth conditions. However the HSC (characterised by the phenotype Lin-, CD38-, CD34+, CD45RA-, CD133+, CD90+, CD49f+) cell expansion is 300 times higher in cells grown in scriptaid and WR1065 compared to cells grown in basal media with cytokines FIG. 6.

Example 4 Expansion of Cells Using Class I HDAC Inhibitors RG2833 and RGFP966

Figure 7:
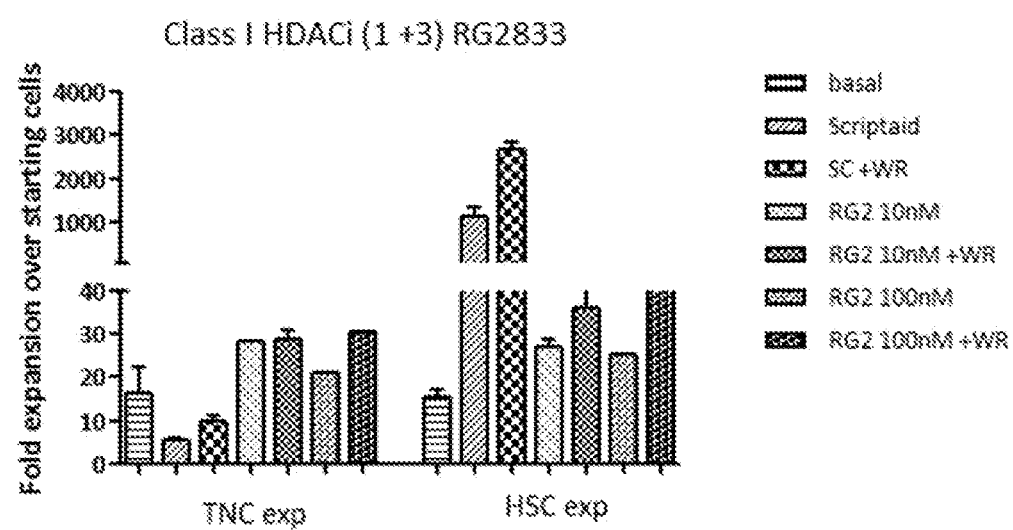
FIG. 7 shows the effect of the class I HDAC inhibitor RG2833 on cell expansion. The fold expansion of TNC and HSC is shown for cells grown under the conditions; media supplemented with cytokines (basal), media supplement with cytokines and scriptaid (scriptaid), media supplemented with cytokines, scriptaid and WR1065 (SC+WR), media supplemented with cytokines and 10 nM RG2833 (RG2 10 nM), media supplemented with cytokines, 10 nM RG2833 and WR1065 (RG2 10 nM+WR), media supplemented with cytokines and 100 nM RG2833 (RG2 100 nM), media supplemented with cytokines, 100 nM RG2833 and WR1065 (RG2 100 nM+WR).

The expansion protocol as defined above was performed using the class I HDAC inhibitors RG2833 and RGFP966. RG2833 is selective for HDAC 1 and 3 and RGFP966 is selective for HDAC 3. Cells were expanded in media containing cytokines (basal), basal media containing either RG2833 or RGFP966, and basal media containing either RG2833 and WR1065 or RGFP966 and WR1065. FIG. 7 shows the expansion of TNC and the expansion of HSC of cells grown in basal media, media containing RG2833, media containing RG2833 and WR1065 (the expansion data for cells grown in media treated with scriptaid and media containing scriptaid and WR1065 is also shown as a comparison). The fold expansion of TNC is shown to increase when treated with RG2833 or with RG2833 and WR1065, when compared to cells grown in basal media. The fold expansion of HSC is also doubled for cells treated with RG2833 or with RG2833 and WR1065, compared to cells grown in basal media. It should also be noted that the cells treated with RG2833 and WR1065 show an increased fold expansion in HSC, compared to the cells treated with RG2833 alone.

Figure 8:
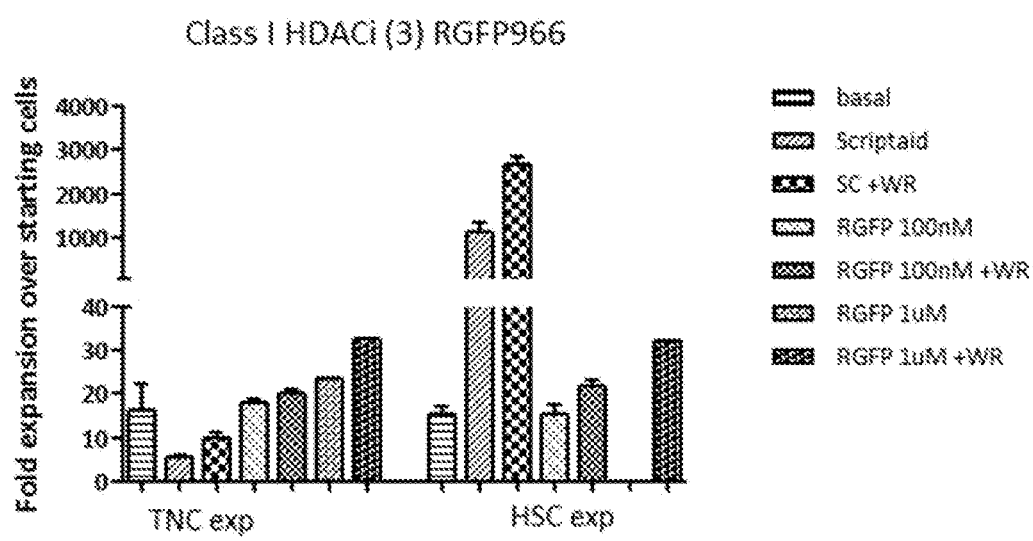
FIG. 8 shows the effect of the class I HDAC inhibitor RGFP966 on cell expansion. The fold expansion of TNC and HSC is shown for cells grown under the conditions; media supplemented with cytokines (basal), media supplement with cytokines and scriptaid (scriptaid), media supplemented with cytokines, scriptaid and WR1065 (SC+WR), media supplemented with cytokines and 100 nM RGFP966 (RGFP 100 nM), media supplemented with cytokines, 100 nM RGFP966 and WR1065 (RGFP 100 nM+WR), media supplemented with cytokines and 1 μM RGFP966 (RGFP 1 μM), media supplemented with cytokines, 1 μM RGFP966 and WR1065 (RGFP 1 μM+WR).

FIG. 8 shows the expansion of TNC and the expansion of HSC of cells grown in basal media, media containing RGFP966, media containing RGFP966 and WR1065 (the expansion data for cells grown in media containing scriptaid and media containing scriptaid and WR1065 is also shown as a comparison). The fold expansion of TNC is shown to increase when treated with RGFP966 or with RGFP966 and WR1065, when compared to cells grown in basal media. The fold expansion of HSC is similar for cells treated with RGFP966 or with RGFP966 and WR1065, compared to cells grown in basal media. However it should be noted that the cells treated with RGFP966 and WR1065 show an increased fold expansion in HSC, compared to the cells treated with RGFP966 alone.

These examples show that cells treated with the class I HDAC inhibitor and WR1065 show an increased fold expansion of the TNC compared to cells grown in basal media. The cells treated with the class I HDAC inhibitor and WR1065 also show an increased fold expansion of the HSC compartment above that seen in cells grown in basal media or treated with the class I HDAC inhibitor alone.

Example 5 Expansion of Cells Using Class IIa HDAC Inhibitor LMK235

Figure 9:
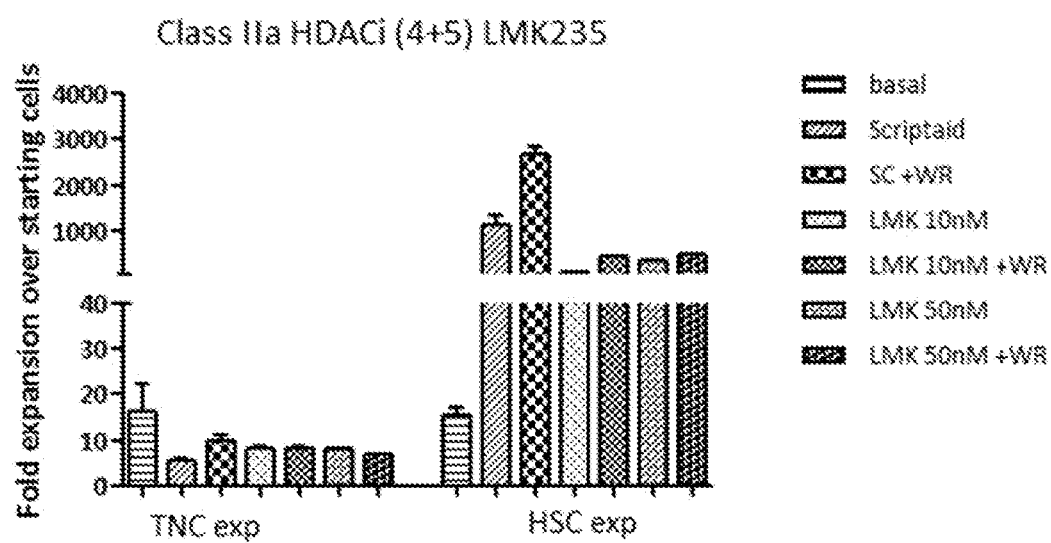
FIG. 9 shows the effect of the class IIa HDAC inhibitor LMK235 on cell expansion. The fold expansion of TNC and HSC is shown for cells grown under the conditions; media supplemented with cytokines (basal), media supplement with cytokines and scriptaid (scriptaid), media supplemented with cytokines, scriptaid and WR1065 (SC+WR), media supplemented with cytokines and 10 nM LMK235

The expansion protocol as defined above was performed using a class IIa HDAC inhibitor LMK235. LMK235 is selective for HDAC 4 and 5. FIG. 9 shows the expansion of TNC and the expansion of HSC of cells expanded in media containing cytokines (basal), basal media containing LMK235, and basal media containing LMK235 and WR1065 (the expansion data for cells grown in media containing scriptaid and media containing scriptaid and WR1065 is also shown as a comparison). The fold expansion of TNC when treated with LMK235 or with LMK235 and WR1065 is slightly lower than the cells grown in basal media. However, the fold expansion of HSC is significantly increased for cells treated with LMK235 or with LMK235 and WR1065, compared to cells grown in basal media.

Example 6 Expansion of Cells Using Class IIb HDAC Inhibitor Tubastatin A

The expansion protocol as defined above was performed using a class IIb HDAC inhibitor Tubastatin A. Tubastatin A is selective for HDAC 6. FIG. 10 shows the expansion of TNC and the expansion of HSC of cells expanded in media containing cytokines (basal), basal media containing Tubastatin A, and basal media containing Tubastatin A and WR1065 (the expansion data for cells grown in media containing scriptaid and media containing scriptaid and WR1065 is also shown as a comparison). The fold expansion of TNC when treated with Tubastatin A or with Tubastatin A and WR1065 is similar than the cells grown in basal media. However, the fold expansion of HSC is significantly increased for cells treated with Tubastatin A and Tubastatin A and WR1065, compared to cells grown in basal media. It should also be noted that the cells treated with the combination of Tubastatin A and WR1065 show an increase in fold expansion of HSC over the cells treated with Tubastatin A alone.

Example 7 Expansion of Cells Using a Broad Spectrum HDAC Inhibitors Sodium Phenylbutyrate and Quisinostat The expansion protocol as defined above was performed using the broad spectrum HDAC inhibitors sodium phenylbutyrate and quisinostat. Sodium phenylbutyrate is currently used to treat urea cycle disorders and quisinostat is currently in clinical trials for use in cancer. Cells were expanded in media containing cytokines (basal), basal media containing either sodium phenylbutyrate or quisinostat, and basal media containing either sodium phenylbutyrate and WR1065 or quisinostat and WR1065. FIG. 11 shows the expansion of TNC and the expansion of HSC of cells grown in basal media, media containing sodium phenylbutyrate, media containing sodium phenylbutyrate and WR1065 (the expansion data for cells grown in media containing scriptaid and media containing scriptaid and WR1065 is also shown as a comparison). The fold expansion of TNC is shown to increase when treated with sodium phenylbutyrate or with sodium phenylbutyrate and WR1065, when compared to cells grown in basal media. The fold expansion of HSC is also increased for cells treated with sodium phenylbutyrate or with sodium phenylbutyrate and WR1065, compared to cells grown in basal media.

FIG. 12 shows the expansion of TNC and the expansion of HSC of cells grown in basal media, media containing quisinostat, media containing quisinostat and WR1065 (the expansion data for cells grown in media containing scriptaid and media containing scriptaid and WR1065 is also shown as a comparison). The fold expansion of TNC is slightly lower for cells treated with quisinostat or with quisinostat and WR1065, when compared to cells grown in basal media. However the fold expansion of HSC is significantly increased for cells treated with quisinostat or with quisinostat and WR1065, compared to cells grown in basal media. It should also be noted that the cells treated with quisinostat and WR1065 show an increased fold expansion in HSC, compared to the cells treated with quisinostat alone.

Example 8 Expansion of Cells from Individual Donors Using Scriptaid and WR1065

The expansion protocol as defined above was performed of UCB cells from three separate donors, as well as a pooled sample of cells. The cells were expanded in media supplemented with cytokines (basal) media containing scriptaid and media containing scriptaid plus WR1065. FIG. 13 shows the fold expansion of HSC was on average 30 fold (range 10-55) higher for the cells treated with scriptaid, when compared to the cells cultured on basal media. Cell treated with the combination of scriptaid and WR1065 showed a two-fold increase in fold expansion of HSC, regardless of fold expansion on scriptaid alone. Although donor variation is present, the combination treatment enhances the expansion of HSCs on all donors tested.

Example 9 Expansion of Cells Using Various Tissue Culture Plates

The combination treatment of scriptaid and WR1065 enhances the expansion of HSCs cells regardless of the type of surface used to grow the cells. The use of scaffolds in cell culture is known to better mimic in vivo conditions and consequently provide a better niche for cells to grow. All previous examples were performed using Nanex plates which comprise a thin scaffold material made of PES electrospun fibres treated with a surface amination. Experiments were performed to show that treatment with scriptaid and WR1065 enhances the expansion of HSC when cells are cultured using standard tissue culture treated plates as well as Nanex plates. The cell expansion protocol was performed as described above and cells were seeded at the same densities onto 3 types of surfaces; Nanex scaffolds, TC treated Corning 24 well plates or suspension Greiner Bio 24 well plates. The fold expansion of HSCs for cells cultured in media supplemented with cytokines (basal) is significantly higher for cells grown in Nanex plates. However, fold expansion of HSC is significantly increased for cells treated with either scriptaid or the combination treatment when compared to cells cultured in basal media. This effect is similar across all surfaces used and the small differences are statistically non-significant.

The invention claimed is:

1. A method to expand hematopoietic stem and progenitor cells (HSPC) wherein the method comprises;
   i) obtaining an isolated population of HSPC
   ii) culturing the isolated population of HSPC in the presence of a histone deacetylase inhibitor (HDAC inhibitor), to form a cultured population
   iii) adding an aminothiol compound having the formula $RNH(C_nH_{2n})NH(C_nH_{2n})SX$, wherein R is hydrogen, an aryl, an acyl, or an alkyl group containing from 1 to 7 carbon atoms, each n has a value of from 2 to 6 and X is H or $PO_3H_2$; or a pharmaceutically acceptable salt thereof, to the cultured population of HSPC to form expanded cells.

2. The method of claim 1, wherein step i) comprises selecting for cells which are CD133+.

3. The method of claim, wherein step i) comprises selecting for cells which are CD34+.

4. The method of claim 1, wherein the HDAC inhibitor is scriptaid or quisinostat.

5. The method of claim 1, wherein the HDAC inhibitor is scriptaid.

6. The method of claim 1, wherein the aminothiol compound is amifostine:

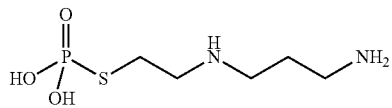

or WR1065:

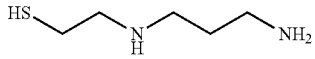

7. The method of claim 1, wherein the aminothiol compound is WR1065.

8. The method of claim 1, wherein the isolated population is obtained from umbilical cord blood.

9. The method of claim 1, wherein the isolated population is obtained from peripheral blood.

10. The method of claim 1, wherein the isolated population obtained from bone marrow.

11. The method of claim 1, wherein the steps ii) and iii) are carried out over a total time of 5 to 10 days to form expanded cells.

12. The method of claim 1, wherein the cells are cultured in a serum free or feeder free tissue culture system.

13. The method of claim 1, wherein the cells are obtained from a mammal, preferably a human.

14. The method of claim 1, wherein the expanded cells are enriched for HSC.

15. The method of claim 1, wherein the expanded cells are enriched for; Lin−, CD38−, CD34+, CD133+, CD45RA−, CD90+ and CD49f+.

16. The method of claim 1, wherein the total cell expansion is between about 2-fold to about 20-fold.

17. The method of claim 1, wherein the expansion of Lin−, CD38−, CD34+, CD133+, CD45RA−, CD90+ and CD49f+ cells is about 500-fold.

18. The method of claim 1, wherein the HDAC inhibitor is used at a concentration of 0.01-50 µM.

19. The method of claim 1, wherein the aminothiol compound is used at a concentration of 50-500 µM.

* * * * *